United States Patent
Zhu et al.

(10) Patent No.: US 9,320,505 B2
(45) Date of Patent: *Apr. 26, 2016

(54) APPARATUS FOR CLOSING VASCULAR PUNCTURE

(71) Applicant: Loma Linda University Medical Center, Loma Linda, CA (US)

(72) Inventors: Yong Hua Zhu, Redlands, CA (US); Wolff M. Kirsch, Redlands, CA (US)

(73) Assignee: Loma Linda University, Loma Linda, CA (US)

( * ) Notice: Subject to any disclaimer, the term of this patent is extended or adjusted under 35 U.S.C. 154(b) by 150 days.

This patent is subject to a terminal disclaimer.

(21) Appl. No.: 14/194,354

(22) Filed: Feb. 28, 2014

(65) Prior Publication Data

US 2014/0180335 A1 Jun. 26, 2014

Related U.S. Application Data

(60) Continuation of application No. 13/849,387, filed on Mar. 22, 2013, now Pat. No. 8,702,750, which is a continuation of application No. 11/098,197, filed on Apr. 4, 2005, now Pat. No. 8,425,552, which is a (Continued)

(51) Int. Cl.
*A61B 17/08* (2006.01)
*A61B 17/00* (2006.01)

(52) U.S. Cl.
CPC ....... *A61B 17/0057* (2013.01); *A61B 17/00491* (2013.01); *A61B 2017/00637* (2013.01); *A61B 2017/00654* (2013.01); *A61B 2017/00659* (2013.01)

(58) Field of Classification Search
CPC ................. A61B 17/0057; A61B 2017/00637; A61B 2017/00654; A61B 2017/00659
See application file for complete search history.

(56) References Cited

U.S. PATENT DOCUMENTS

| 1,064,307 A | 6/1913 | Fleming |
| 3,483,870 A | 12/1969 | Coover et al. |

(Continued)

FOREIGN PATENT DOCUMENTS

| CA | 2334226 | 4/2005 |
| CA | 2274066 | 2/2006 |

(Continued)

OTHER PUBLICATIONS

Angio-Seal, Hemostasis Puncture Closure Device Brochure, Sherwood Medical Co., Jun. 11, 1997.

(Continued)

*Primary Examiner* — Gregory Anderson
(74) *Attorney, Agent, or Firm* — Knobbe Martens Olson & Bear, LLP

(57) ABSTRACT

A method and apparatus for closing a vascular wound includes a guidewire and/or other surgical implement extending from the wound. A hemostatic material is advanced over the surgical implement and into contact with an area of the blood vessel surrounding the wound. The surgical implement is removed. Blood soaks the hemostatic material, and blood clotting is facilitated by the hemostatic agent within the material. A sealing layer of adhesive can be applied to the hemostatic material, confining the blood flow to the material. The vascular puncture wound is sealed by natural blood clot formation.

20 Claims, 17 Drawing Sheets

Related U.S. Application Data division of application No. 09/921,158, filed on Aug. 1, 2001, now Pat. No. 6,890,342.

(60) Provisional application No. 60/222,525, filed on Aug. 2, 2000.

(56) References Cited

U.S. PATENT DOCUMENTS

| | | |
|---|---|---|
| 3,518,993 A | 7/1970 | Blake |
| 3,653,388 A | 4/1972 | Tenckhoff |
| 3,893,454 A | 7/1975 | Hagelin |
| 3,920,021 A | 11/1975 | Hiltebrandt |
| 4,306,562 A | 12/1981 | Osborne |
| 4,317,445 A | 3/1982 | Robinson |
| 4,325,376 A | 4/1982 | Klieman et al. |
| 4,351,466 A | 9/1982 | Noiles |
| 4,487,204 A | 12/1984 | Hrouda |
| 4,492,232 A | 1/1985 | Green |
| 4,530,698 A | 7/1985 | Goldstein et al. |
| 4,532,134 A | 7/1985 | Malette et al. |
| 4,534,351 A | 8/1985 | Rothfuss et al. |
| 4,539,990 A | 9/1985 | Stivala |
| 4,585,437 A | 4/1986 | Simms |
| 4,611,595 A | 9/1986 | Klieman et al. |
| 4,616,650 A | 10/1986 | Green et al. |
| 4,622,970 A | 11/1986 | Wozniak |
| 4,651,725 A | 3/1987 | Kifune et al. |
| 4,738,658 A | 4/1988 | Magro et al. |
| 4,772,266 A | 9/1988 | Groshong |
| 4,821,719 A | 4/1989 | Fogarty |
| 4,865,593 A | 9/1989 | Ogawa et al. |
| 4,889,112 A | 12/1989 | Schachner et al. |
| 4,890,612 A | 1/1990 | Kensey |
| 4,900,303 A | 2/1990 | Lemelson |
| 4,905,267 A | 2/1990 | Miller et al. |
| 4,917,087 A | 4/1990 | Walsh et al. |
| 4,921,479 A | 5/1990 | Grayzel |
| 4,930,674 A | 6/1990 | Barak |
| 4,931,058 A | 6/1990 | Cooper |
| 4,934,364 A | 6/1990 | Green |
| 4,961,729 A | 10/1990 | Vaillancourt |
| 4,984,564 A | 1/1991 | Yuen |
| 4,999,235 A | 3/1991 | Lunn et al. |
| 5,002,557 A | 3/1991 | Hasson |
| 5,006,106 A | 4/1991 | Angelchik |
| 5,015,249 A | 5/1991 | Nakato et al. |
| 5,057,083 A | 10/1991 | Gellman |
| 5,114,400 A | 5/1992 | Lynn |
| 5,147,381 A | 9/1992 | Heimerl et al. |
| 5,176,128 A | 1/1993 | Andrese |
| 5,176,129 A | 1/1993 | Smith |
| 5,192,301 A | 3/1993 | Kamiya et al. |
| 5,192,302 A | 3/1993 | Kensey et al. |
| 5,242,387 A | 9/1993 | Loughlin |
| 5,257,979 A | 11/1993 | Jagpal |
| 5,259,835 A | 11/1993 | Clark et al. |
| 5,282,827 A | 2/1994 | Kensey et al. |
| 5,290,310 A | 3/1994 | Makower et al. |
| 5,292,332 A | 3/1994 | Lee |
| 5,297,714 A | 3/1994 | Kramer |
| 5,300,065 A | 4/1994 | Anderson |
| 5,306,254 A | 4/1994 | Nash et al. |
| 5,306,259 A | 4/1994 | Fischell et al. |
| 5,312,355 A | 5/1994 | Lee |
| 5,320,639 A | 6/1994 | Rudnick |
| 5,324,306 A | 6/1994 | Makower et al. |
| 5,342,393 A | 8/1994 | Stack |
| 5,350,399 A | 9/1994 | Erlebacher et al. |
| 5,352,207 A | 10/1994 | Nussbaum |
| 5,360,397 A | 11/1994 | Pinchuk |
| 5,370,660 A | 12/1994 | Weinstein et al. |
| 5,383,896 A | 1/1995 | Gershony et al. |
| 5,383,899 A | 1/1995 | Hammerslag |
| 5,391,183 A | 2/1995 | Janzen et al. |
| 5,397,311 A | 3/1995 | Walker et al. |
| 5,407,427 A | 4/1995 | Zhu et al. |
| 5,411,520 A | 5/1995 | Nash et al. |
| 5,417,699 A | 5/1995 | Klein et al. |
| 5,419,765 A | 5/1995 | Weldon et al. |
| 5,423,814 A | 6/1995 | Zhu et al. |
| 5,425,746 A | 6/1995 | Proto et al. |
| 5,431,639 A | 7/1995 | Shaw |
| 5,437,631 A | 8/1995 | Janzen |
| 5,443,484 A | 8/1995 | Kirsch et al. |
| 5,445,597 A | 8/1995 | Clark et al. |
| 5,460,621 A | 10/1995 | Gertzman et al. |
| 5,480,380 A | 1/1996 | Martin |
| 5,486,195 A | 1/1996 | Myers et al. |
| 5,529,577 A | 6/1996 | Hammerslag |
| 5,531,759 A | 7/1996 | Kensey et al. |
| 5,536,251 A | 7/1996 | Evard et al. |
| 5,545,178 A | 8/1996 | Kensey et al. |
| 5,556,375 A | 9/1996 | Ewall |
| 5,620,461 A | 4/1997 | Muijs Van De Moer et al. |
| 5,632,727 A | 5/1997 | Tipton et al. |
| 5,643,318 A | 7/1997 | Tsukernik et al. |
| 5,645,566 A | 7/1997 | Brenneman et al. |
| 5,649,911 A | 7/1997 | Trerotola |
| 5,649,959 A | 7/1997 | Hannam et al. |
| 5,653,730 A | 8/1997 | Hammerslag |
| 5,658,298 A | 8/1997 | Vincent et al. |
| 5,662,681 A | 9/1997 | Nash et al. |
| 5,665,106 A | 9/1997 | Hammerslag |
| 5,665,107 A | 9/1997 | Hammerslag |
| 5,674,231 A | 10/1997 | Green et al. |
| 5,676,689 A | 10/1997 | Kensey et al. |
| 5,684,042 A | 11/1997 | Greff et al. |
| 5,725,551 A | 3/1998 | Myers et al. |
| 5,728,114 A | 3/1998 | Evans |
| 5,728,132 A | 3/1998 | Van Tassel et al. |
| 5,755,693 A | 5/1998 | Walker et al. |
| 5,759,169 A | 6/1998 | Marx |
| 5,759,194 A | 6/1998 | Hammerslag |
| 5,776,096 A | 7/1998 | Fields |
| 5,810,810 A | 9/1998 | Tay et al. |
| 5,811,091 A | 9/1998 | Greff et al. |
| 5,836,970 A | 11/1998 | Pandit |
| 5,843,124 A | 12/1998 | Hammerslag |
| 5,876,387 A | 3/1999 | Killian et al. |
| 5,895,412 A | 4/1999 | Tucker |
| 5,906,631 A | 5/1999 | Imran |
| 5,910,155 A | 6/1999 | Ratcliff et al. |
| 5,928,266 A | 7/1999 | Kontos |
| 5,944,730 A | 8/1999 | Nobles et al. |
| 5,971,956 A | 10/1999 | Epstein |
| 6,004,341 A | 12/1999 | Zhu et al. |
| 6,007,563 A | 12/1999 | Nash et al. |
| 6,016,806 A | 1/2000 | Webb |
| 6,033,413 A | 3/2000 | Mikus et al. |
| 6,048,358 A | 4/2000 | Barak |
| 6,056,768 A | 5/2000 | Cates et al. |
| 6,110,184 A | 8/2000 | Weadock |
| 6,155,265 A | 12/2000 | Hammerslag |
| 6,159,178 A | 12/2000 | Sharkaway et al. |
| 6,197,042 B1 | 3/2001 | Ginn et al. |
| 6,198,016 B1 | 3/2001 | Lucast et al. |
| 6,277,140 B2 | 8/2001 | Ginn et al. |
| 6,287,322 B1 | 9/2001 | Zhu et al. |
| 6,287,323 B1 | 9/2001 | Hammerslag |
| 6,315,753 B1 | 11/2001 | Cragg et al. |
| 6,325,789 B1 | 12/2001 | Janzen et al. |
| 6,346,093 B1 | 2/2002 | Allman et al. |
| 6,371,974 B1 | 4/2002 | Brenneman |
| 6,391,048 B1 | 5/2002 | Ginn et al. |
| 6,425,901 B1 | 7/2002 | Zhu et al. |
| 6,461,364 B1 | 10/2002 | Ginn et al. |
| 6,508,828 B1 | 1/2003 | Akerfeldt et al. |
| 6,524,326 B1 | 2/2003 | Zhu et al. |
| 6,589,269 B2 | 7/2003 | Zhu et al. |
| 6,613,070 B2 | 9/2003 | Redmond et al. |
| 6,632,238 B2 | 10/2003 | Ginn et al. |
| 6,649,162 B1 | 11/2003 | Biering et al. |
| 6,890,342 B2 | 5/2005 | Zhu et al. |
| 6,964,675 B2 | 11/2005 | Zhu et al. |

(56) References Cited

U.S. PATENT DOCUMENTS

| | | |
|---|---|---|
| 6,966,896 B2 | 11/2005 | Kurth et al. |
| 7,303,552 B1 | 12/2007 | Chu et al. |
| 2001/0004710 A1 | 6/2001 | Felt et al. |
| 2001/0018598 A1 | 8/2001 | Cruise et al. |
| 2002/0002386 A1 | 1/2002 | Ginn et al. |
| 2002/0022822 A1 | 2/2002 | Cragg et al. |
| 2002/0072767 A1 | 6/2002 | Zhu |
| 2002/0072768 A1 | 6/2002 | Ginn |
| 2002/0077656 A1 | 6/2002 | Ginn et al. |
| 2002/0077657 A1 | 6/2002 | Ginn et al. |
| 2002/0147479 A1 | 10/2002 | Aldrich |
| 2003/0023267 A1 | 1/2003 | Ginn |
| 2003/0045893 A1 | 3/2003 | Ginn |
| 2003/0050665 A1 | 3/2003 | Ginn |
| 2003/0078598 A1 | 4/2003 | Ginn et al. |
| 2003/0109820 A1 | 6/2003 | Gross et al. |
| 2003/0125654 A1 | 7/2003 | Malik |
| 2003/0158577 A1 | 8/2003 | Ginn et al. |
| 2003/0158578 A1 | 8/2003 | Pantages et al. |
| 2003/0167050 A1 | 9/2003 | Prosl et al. |
| 2005/0209637 A1 | 9/2005 | Zhu et al. |
| 2007/0123816 A1 | 5/2007 | Zhu et al. |

FOREIGN PATENT DOCUMENTS

| | | |
|---|---|---|
| EP | 0028452 A1 | 5/1981 |
| EP | 0482350 A2 | 4/1992 |
| EP | 0646350 A1 | 4/1995 |
| EP | 0745350 A1 | 12/1996 |
| EP | 0788769 A1 | 8/1997 |
| EP | 0818178 A2 | 1/1998 |
| EP | 0955900 B1 | 7/2005 |
| GB | 2318295 A | 4/1998 |
| JP | H6-339483 | 12/1994 |
| JP | H10-43311 | 2/1998 |
| JP | 11-128360 | 5/1999 |
| WO | WO 9421306 A1 | 9/1994 |
| WO | WO 9505206 A2 | 2/1995 |
| WO | WO 9610374 A1 | 4/1996 |
| WO | WO 9624291 A1 | 8/1996 |
| WO | WO 9720505 A1 | 6/1997 |
| WO | WO 9824374 A1 | 6/1998 |
| WO | WO 9920326 | 4/1999 |
| WO | WO 9930685 A1 | 6/1999 |
| WO | WO 9942535 A1 | 8/1999 |
| WO | WO 9962405 A1 | 12/1999 |
| WO | WO 0002488 A1 | 1/2000 |
| WO | WO 0007640 A2 | 2/2000 |
| WO | WO 0019912 A1 | 4/2000 |
| WO | WO 0033744 A1 | 6/2000 |
| WO | WO 0134238 A1 | 5/2001 |
| WO | WO 0162159 A2 | 8/2001 |
| WO | WO 0205865 A2 | 1/2002 |
| WO | WO 0209591 A2 | 2/2002 |
| WO | WO 03008002 A1 | 1/2003 |
| WO | WO 03008003 A1 | 1/2003 |
| WO | WO 2007/044510 | 4/2007 |

OTHER PUBLICATIONS

Gershony, Gary, M.D., A Novel Femoral Access Site Closure Device: Duet, Early European Clinical Trials, Los Angeles Cardiology Associates, Seminar, Coronary Interventions, Oct. 16-18, 1997.

Medafor, Inc. "Medafor, Inc. Adds Two management Team Members", Press Release, Jun. 7, 2001, http://www.medafor.com/news0601.html.

Medafor, Inc. "Microporous Polysaccharide Hemospheres Provides Effective Topical Hemostasis in a Human Modified Bleeding Time Incision Model", Sep. 2002.

APPARATUS FOR CLOSING VASCULAR PUNCTURE

INCORPORATION BY REFERENCE TO RELATED APPLICATIONS

Any and all priority claims identified in the Application Data Sheet, or any correction thereto, are hereby incorporated by reference under 37 CFR 1.57. This application is a continuation of U.S. application Ser. No. 13/849,387 filed on Mar. 22, 2013, which is a continuation of U.S. application Ser. No. 11/098,197 filed on Apr. 4, 2005, now U.S. Pat. No. 8,425,552, which is a divisional of U.S. application Ser. No. 09/921,158 filed on Aug. 1, 2001, now U.S. Pat. No. 6,890,342, which claims priority to U.S. Application Ser. No. 60/222,525 filed on Aug. 2, 2000. Each of the aforementioned applications is incorporated by reference herein in its entirety, and each is hereby expressly made a part of this specification.

FIELD OF THE INVENTION

The present invention generally relates to a system that facilitates closure of openings in blood vessels. More specifically, the present device delivers a hemostatic material to the opening to facilitate sealing of the blood vessel wound.

BACKGROUND OF THE INVENTION

In many medical procedures, it is necessary to locate an opening in tissue so that some form of treatment, diagnosis or revision, can be applied to that opening. For example, in order to perform transluminal balloon angioplasty, an opening must be created in an artery in order to insert a balloon. This opening must later be closed.

Transluminal balloon angioplasty is used in the treatment of peripheral vascular disease to increase or restore blood flow through a significantly narrowed artery in a limb; it is also used in the treatment of blockage of the coronary arteries. In fact, coronary angioplasty has emerged as a major viable alternative to bypass surgery for revascularization of stenotic and occluded coronary arteries. Unlike bypass surgery, angioplasty does not require general anesthesia, opening of the chest wall, use of a heart-lung machine, or transfusion of blood. Angioplasty is not only less invasive and less traumatic to the patient, it is also less expensive because of the shorter hospital stay and shorter recovery time.

Transluminal balloon angioplasty is performed by first inserting a hollow needle through the skin and surrounding tissues and into the patient's femoral artery. A guidewire is advanced through the hollow needle and into the artery, then along the patient's vasculature toward the site of the blocked blood vessel or heart valve to be treated. X-ray imaging is used to help move the guidewire through the vascular system and into position just past the stenosis to be treated. A balloon catheter is then threaded over the guidewire and advanced until the deflated balloon is within the stenosis. The balloon is then repeatedly inflated to widen the narrowed blood vessel. After the procedure is complete, the catheter and guidewire are withdrawn from the blood vessels and the patient.

Angiography, which is used to detect diseases that alter the appearance of blood vessels, is performed in a similar manner. A hollow needle is first inserted into the femoral artery and a guidewire is inserted through the needle and into the affected blood vessel. A catheter is threaded over the guidewire and into the blood vessel. X-ray imaging is used to guide the catheter to a desired position. Contrast medium is then injected, and a rapid sequence of x-ray pictures are taken so that blood flow along the affected vessel can be studied. The catheter and guidewire are later removed from the patient's body.

After the catheter used during angioplasty or angiography are removed, the puncture wound in the femoral artery must be closed and the bleeding through the puncture site in the artery stopped. Currently, ice packs and/or pressure are applied to the area surrounding the wound for a period lasting up to several hours in an attempt to stop the bleeding. There exists, however, a significant chance that the wound will reopen and begin bleeding again when the patient moves. Another possible complication is the development of a false aneurysm, which increases the risks of both infection and reopening.

Although efforts have been made to close the puncture wound using staples, clips, collagen plugs, and sutures, they have been unsuccessful, largely due to the inability to see the puncture wound in the femoral artery, and also because of the difficulty of controllably modifying the artery in the limited space provided.

Other wounds in the vasculature of a patient can also be difficult to see, and are thus difficult to locate, access and close. Thus, a device and method to facilitate locating and closing of such wounds in the vasculature of a patient would be extremely beneficial. A device having the ability to consistently and reliably locate, isolate and close the puncture wound would eliminate the prolonged bleeding currently associated with such wounds.

SUMMARY OF THE INVENTION

Accordingly, there is a need in the art for a device and method for precisely locating a blood vessel wound and sealing the wound.

In accordance with one embodiment, an assembly for closing a blood vessel wound is provided. An elongate catheter of the assembly accommodates a guidewire threaded therethrough. The catheter is configured to slide over the guidewire so that a tip of the catheter extends into a blood vessel wound. A hemostatic material comprises a hemostasis-facilitating agent. A push member is adapted to slide relative to the catheter. The push member has a lumen adapted to communicate a flowable adhesive therethrough.

In accordance with another embodiment, an assembly is provided for closing a vascular wound. A surgical implement is configured to extend at least partially through a vascular wound. A hemostatic material member comprises a hemostatic agent. A push member is configured to be longitudinally slidable relative to the surgical implement. The push member is adapted to engage and push the hemostatic material longitudinally over the surgical implement.

In accordance with yet another embodiment, an assembly is provided for locating and sealing a vascular puncture. An elongate catheter has a lumen sized and adapted to accommodate a guidewire threaded therethrough. The catheter comprises a distal tip having a first outer diameter and a puncture edge engagement portion proximal of the distal tip and having a second outer diameter greater than the first diameter. The catheter is configured to slide over the guidewire so that a portion of the catheter extends through the vascular puncture. The engagement portion engages edges of the puncture, and is sized to flex the puncture edges sufficient to substantially plug the puncture. A hemostatic sponge is positioned on the catheter proximal of the engagement portion, and is arranged so as to extend substantially circumferentially around an outer surface of the catheter. A retractor is selectively movable between a closed position and an open position. The retractor is configured to engage the outer surface of the catheter when in the closed position and is configured when in the open position to enable the sponge to move longitudinally over the catheter and through the open retractor. A push member is configured to engage the hemostatic sponge and push the sponge distally over the catheter.

For purposes of summarizing the preferred embodiments and the advantages achieved over the prior art, certain embodiments and advantages have been described herein above. Of course, it is to be understood that not necessarily all such advantages may be achieved in accordance with any particular embodiment. Thus, for example, those skilled in the art will recognize that the invention may be embodied or carried out in a manner that achieves or optimizes one advantage or group of advantages as taught herein without necessarily achieving other objects or advantages as may be taught or suggested herein.

The embodiments discussed above and other embodiments will become readily apparent to those skilled in the art from the following detailed description of the preferred embodiments having reference to the attached figures, the invention not being limited to any particular preferred embodiment(s) disclosed.

DETAILED DESCRIPTION OF THE PREFERRED EMBODIMENT

The present apparatus and method is especially useful for closing vascular puncture wounds that are difficult to access and/or visualize. It is difficult to directly and accurately modify the wounded blood vessel in order to close such wounds. Additionally, there are pitfalls associated with directly modifying the blood vessel. For example, since the clinician cannot see the wound, it is difficult to correctly place closure media such as sutures, staples, or clips. Incorrect placement of such closure media likely results in inadequate closure; the puncture wound remains open, perhaps without the clinician being aware. Additionally, incorrect placement of closure media may cause permanent damage to the vessel, including tearing and additional puncture wounds. Further, if closure media extends through the wound and into the blood flow, this media can increase the likelihood of thrombus formation or could introduce potentially toxic substances into the bloodstream. Of course, closure media inadvertently released into the bloodstream could lead to serious blood vessel blockage complications.

Figure 1:
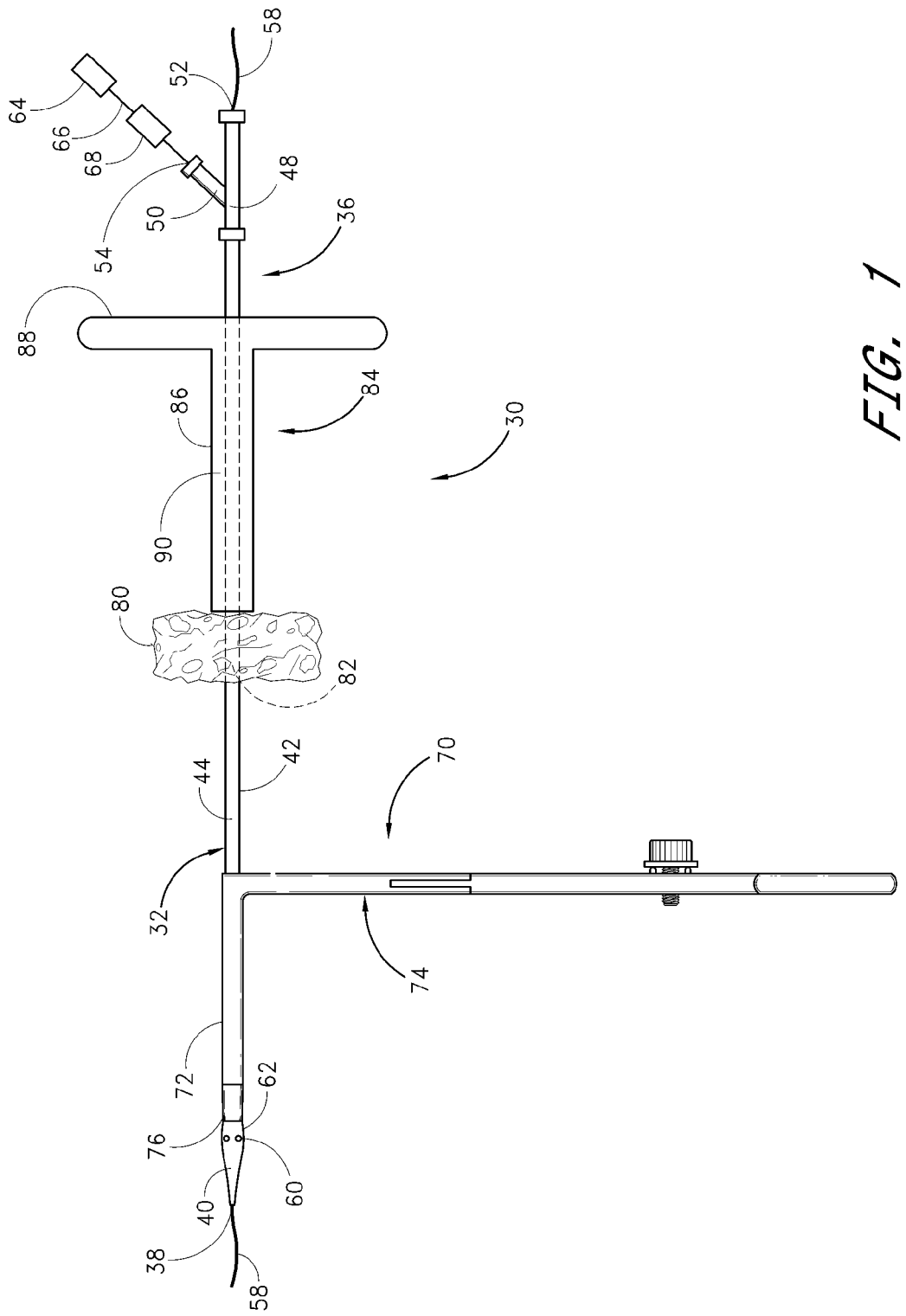
FIG. 1 is a side view of an embodiment of a vascular closure apparatus shown assembled and ready for use.

With reference to FIG. 1, a vascular wound closure assembly 30 includes an elongate catheter 32 having a distal end 34 and a proximal end 36 of the catheter 32. A distal opening 38 is formed through the distal end 34 of the catheter 32 and opens along a longitudinal axis of the catheter 32. The catheter 32 includes a tapered tip 40 at the distal end 34. An elongate main body 42 of the catheter 32 is disposed proximal the tapered tip 40. Preferably the main body 42 has a substantially uniform diameter along its length. A lumen 44 extends longitudinally within the catheter 32 from the distal opening 38 to the proximal end 36.

A connector portion 46 is provided on the proximal end 36. The connector portion 46 includes a main lumen 48 and a secondary lumen 50. The main lumen 48 extends along the longitudinal axis of the catheter 32 and is coextensive with the catheter lumen 44. The secondary lumen 50 extends outwardly from the main lumen 48, but communicates with the main lumen 48 and the catheter lumen 44. A proximal opening 52 is provided at the proximal end of the main lumen 48 and, like the distal opening 38, opens along the longitudinal axis. A secondary opening 54 opens into the secondary lumen 50.

The distal and proximal openings 38, 52 are sized and adapted to accommodate a guidewire 58 such as the guidewire used in angioplasty and other vascular surgeries. As such, the guidewire 58 can be threaded through the catheter 32 and the catheter can be advanced over the guidewire 58.

Holes 60 are formed through a side wall of the catheter 32 near the distal end 34 of the catheter 32. Preferably, at least two holes 60 are provided. All of the holes 60 preferably are disposed substantially the same distance from the distal end 34 of the catheter 32. Preferably, a raised portion 62 of the catheter 32 is provided in the region around the holes 60, which region is proximal of the tip 40 and distal of the main body 42. At the raised portion 62, the catheter 32 has an outer diameter that is slightly larger than the outer diameter throughout the catheter main body 42.

With continued reference to FIG. 1, a vacuum or other source of suction 64 is provided and communicates, through tubing 66, with the secondary lumen 50 of the catheter connector portion 46. Thus, a vacuum is drawn through the catheter lumen 44. Preferably, the distal and proximal openings 38, 52, which accommodate the guidewire 58, are sized so that the guidewire 58 substantially plugs the openings; thus, the vacuum is drawn through the holes 60. A viewing port 68 is arranged between the source of suction 64 and the catheter 32. The viewing port 68 is configured to allow a clinician to view the material that is drawn by suction through the holes 60 and through the catheter lumen 44. The viewing port 68 will be discussed in more detail below.

Figure 2:
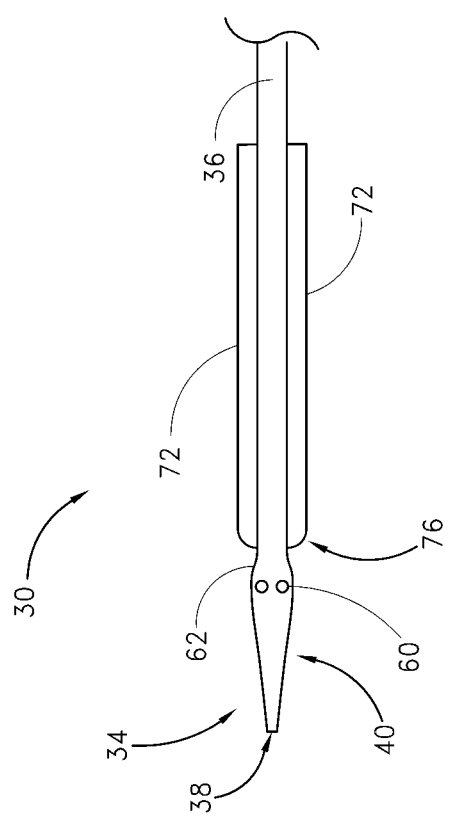
FIG. 2 is a side view of a distal portion of the apparatus of FIG. 1.

With reference to FIGS. 1 and 2, a retractor 70 is preferably mounted on the catheter 32. The retractor 70 includes opposing elongate retractor arms 72 that are aligned longitudinally on the catheter 32. A retractor body 74 is configured to selectively open and close the retractor arms 72 when operated by a clinician. The elongate retractor arms 72 of the retractor 70 are positioned on the catheter 32 so that distal ends 76 of the arms are positioned proximal of the catheter holes 60 a distance that is at least the same as the width of an artery wall, preferably at least about 0.5 to 2 millimeters.

With reference again to FIG. 1, a hemostatic member 80 is arranged on the catheter 32 proximal of the retractor 70. As will be discussed in more detail below, the hemostatic member comprises a material that is made of or includes a hemostatic agent. The hemostatic agent is adapted to aid blood clotting. In one embodiment, the hemostatic member 80 comprises a sponge or sponge-like material. In this description, sponge is a broad term that is used in accordance with it ordinary meaning and includes, without limitation, a material that is adapted to soak up at least a portion of blood that may come in contact with the material.

For purposes of this description, the hemostatic member 80 is referred to as the sponge 80. However, it is to be understood that use of the term "sponge" does not limit the scope of materials that can be used as the hemostatic member. In fact, any material that aids or facilitates blood clotting can be used as the hemostatic member.

Preferably, the sponge 80 extends circumferentially around the catheter main body 42, and is arranged so that it can be slid longitudinally along the catheter 32. Most preferably, the catheter 32 extends through a passageway 82 through the sponge 80. The passageway 82 is formed as the catheter 32 is forced through the sponge 80.

Figure 3:
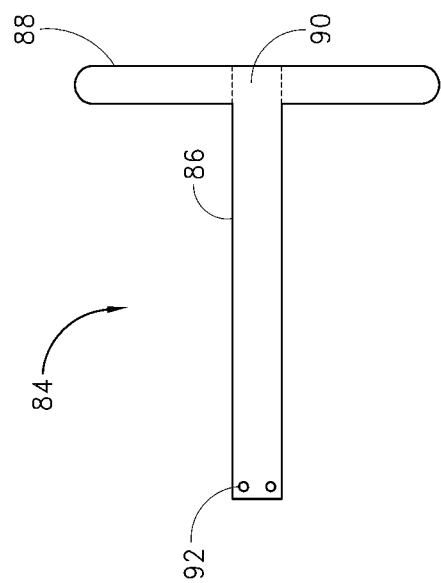
FIG. 3 is a side view of a push member having features in accordance with the present invention.

A push member 84 is also arranged on the catheter 32 distal of the sponge 80. With reference also to FIG. 3, the push member 84 comprises a body portion 86 and a proximal handle portion 88. An elongate lumen 90 is formed through the body portion 86. As shown in FIG. 1, the lumen 90 preferably encircles the catheter 32 so as to allow the push member 84 to slide relative to the catheter 32. A plurality of holes 92 are formed through the body portion 86 at a point near the distal end of the push member 84.

As will be discussed in more detail below in connection with FIG. 4, the vascular wound closure assembly 30 enables a clinician to precisely locate a subcutaneous vascular wound "w", access the wound w, and deliver the hemostatic sponge 80 to the wound site. The hemostatic sponge 80 includes a hemostatic agent that helps facilitate closure of the wound w.

In order to properly apply the hemostatic sponge 80, the vascular closure assembly 30 first precisely locates and provides access to the vascular wound w. It is to be understood that the present method and apparatus can be used to close various vascular and other wounds. FIGS. 1-11, and the accompanying discussion, present an example using an embodiment to close a puncture wound w in a patient's femoral artery 94.

With specific reference to FIGS. 1, 2, 4 and 5, in order to precisely locate and provide access to a femoral artery puncture wound w, the catheter 32 is first threaded over a guidewire 58 that has been previously inserted into the patient's femoral artery 94 through the puncture wound w. The lumen 44 is attached to the source of suction 64 and the assembly 30 is advanced over the guidewire 58 through a patient's tissue 96 so that the distal tip 40 of the catheter 32 extends through the vascular puncture wound w.

As the assembly 30 is advanced, the source of suction 64 draws bodily fluids through the holes 60. The fluids pass through the viewing port 68, which allows the clinician to identify the fluids being withdrawn. The viewing port 68 can have any suitable structure or location. For example, the viewing port can comprise clear tubing attached to the catheter, a substantially transparent syringe that functions as both a source of suction and a viewing port, or a portion of the catheter that is substantially transparent. Most preferably, the catheter 32 is formed of a transparent material so that the clinician becomes aware as soon as blood begins to be drawn through the catheter.

Figure 4:
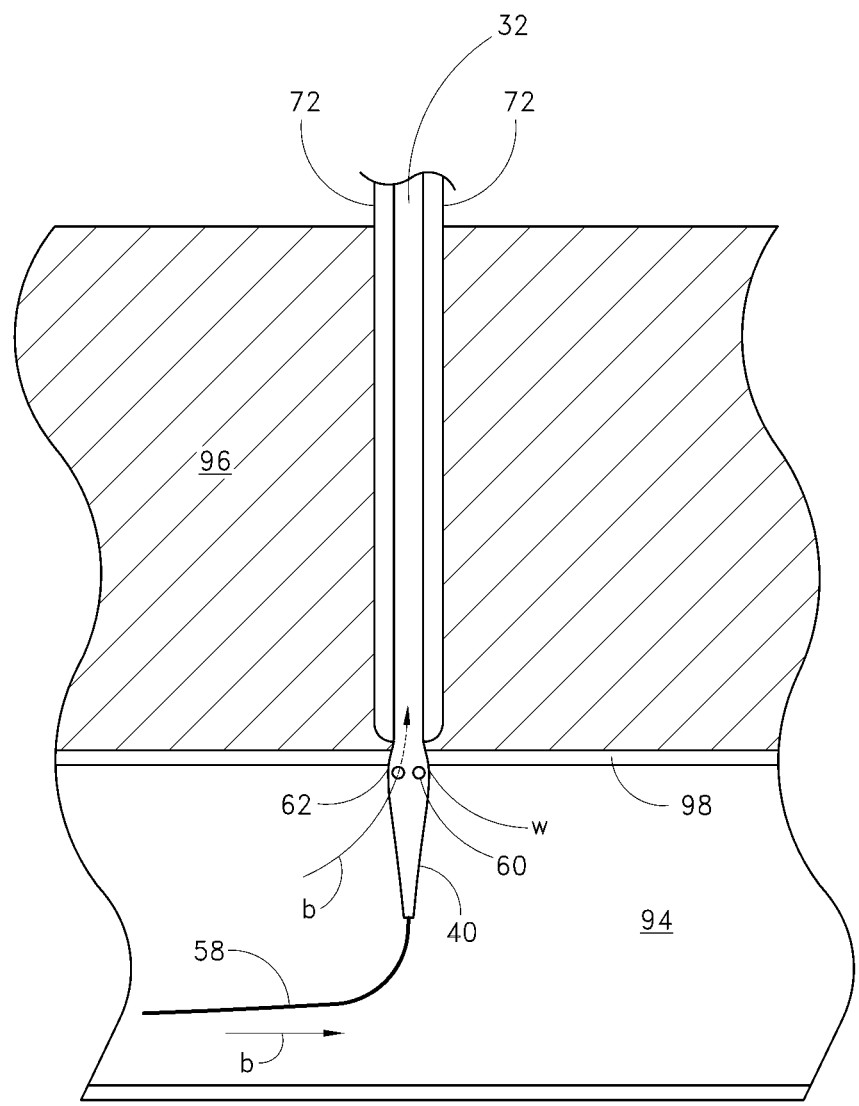
FIG. 4 shows the apparatus of FIG. 1 advanced over a guidewire into a blood vessel of a patient.
Figure 5:
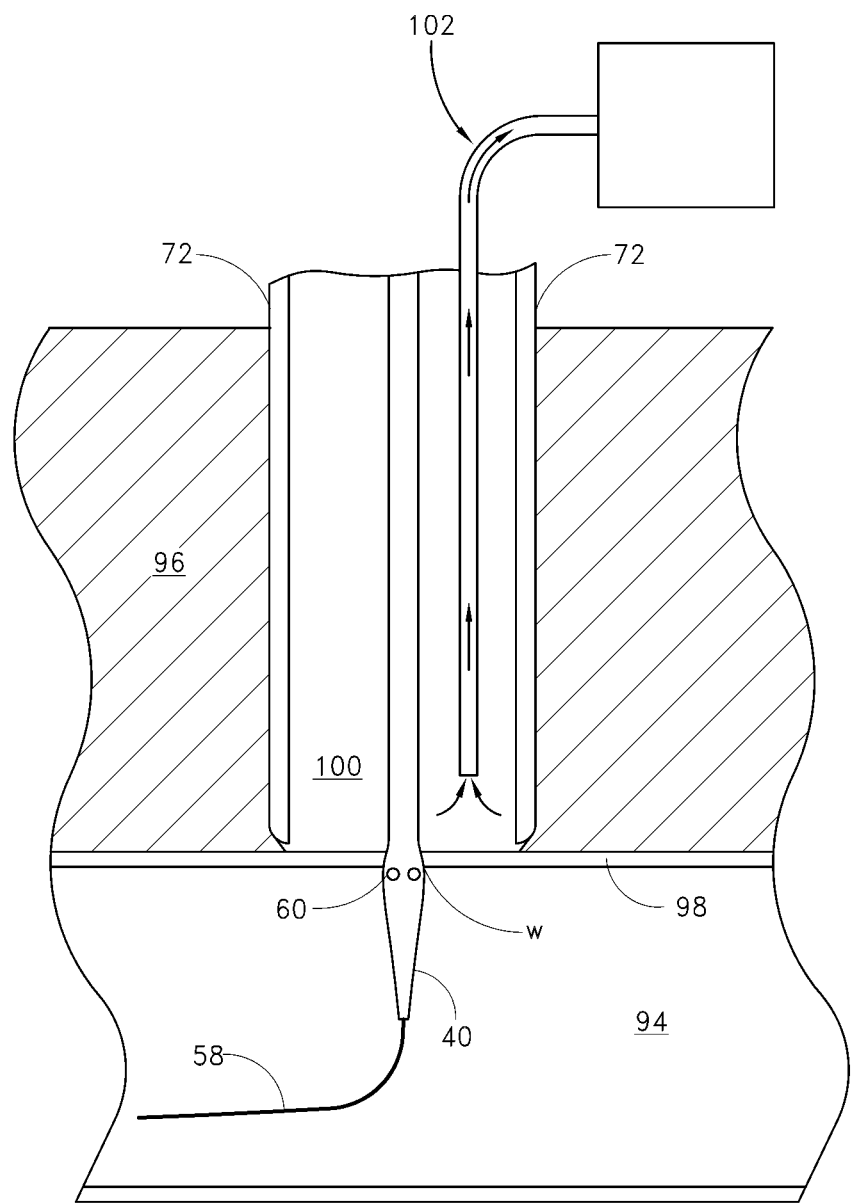
FIG. 5 shows the arrangement of FIG. 4 with the retractor arms open and a suction tool in use.

When the holes 60 pass the artery wall 98 and enter the blood vessel 94, as shown in FIG. 4, blood "b" begins to be drawn through the holes 60 into the catheter 32 and is conducted past the viewing port 68. Thus, when blood b is observed in the viewing port 68, the clinician will know that the holes 60 have just passed into the puncture wound w and that the distal ends 76 of the retractor arms 72 are thus positioned adjacent the outer wall 98 of the artery 94, preferably within about 2 mm of the artery wall 98. The retractor arms 72 are then separated as shown in FIG. 5, thus drawing surrounding tissue 96 away from the wound w and creating a field 100 around the puncture wound w. The catheter 32 remains disposed partially within the puncture wound w, effectively plugging the wound and preventing blood from flowing through the wound. The raised portion 62 flexes the edges of the wound w to enhance the seal between the catheter 32 and the puncture wound edges.

With continued reference to FIG. 5, a suction tool 102 can be used to clear away bodily fluids and other matter that may be within the field 100 and to clean the wall 98 of the blood vessel 94 adjacent the puncture wound w.

Figure 6:
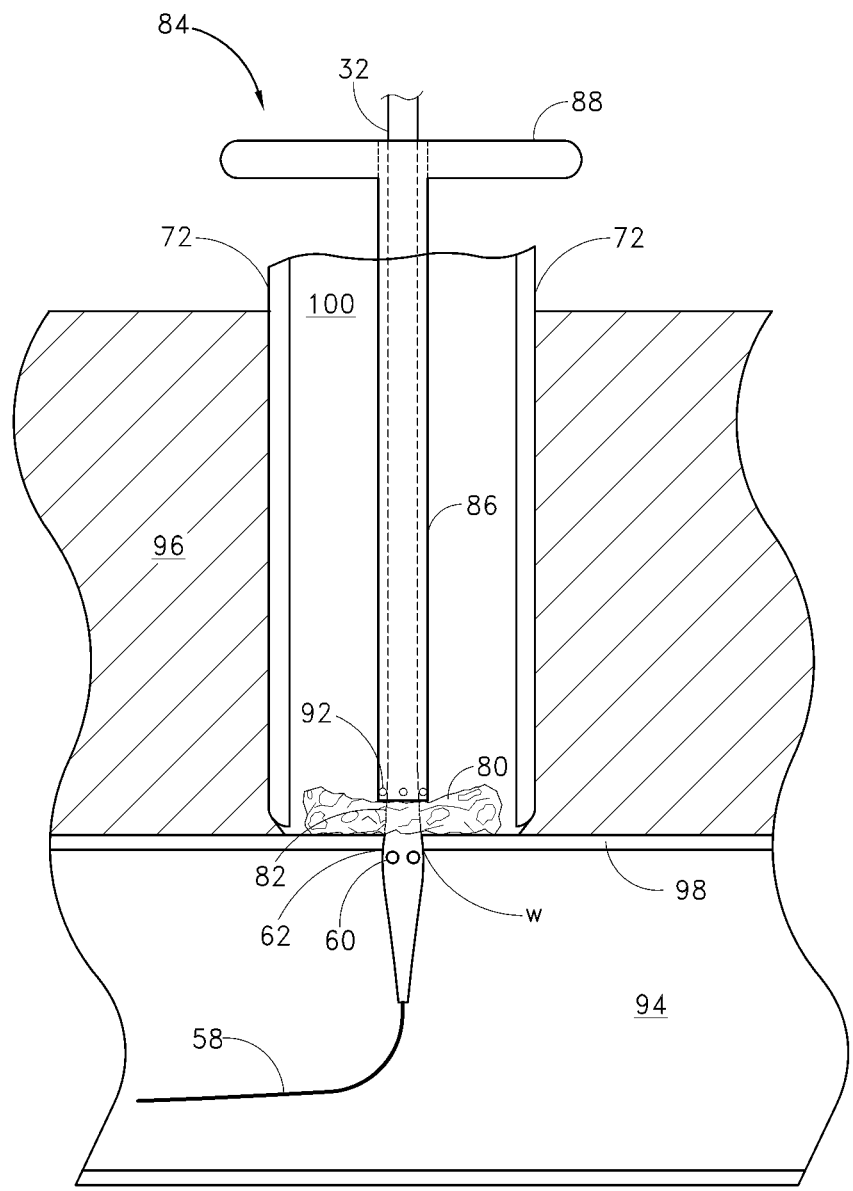
FIG. 6 shows the arrangement of FIG. 5, wherein a hemostatic sponge has been advanced into contact with the blood vessel wall.

With reference next to FIG. 6, once the puncture wound w has been precisely located, the push member 84 is advanced distally along the catheter 32, thus advancing the sponge 80 into contact with the vessel wall 98 so as to surround the puncture wound w. As mentioned above and discussed in more detail below, the sponge 80 comprises a hemostatic agent that will help accelerate blood clot formation at the wound site w in order to help the wound heal faster.

With particular reference to FIGS. 1 and 6, in the illustrated embodiment an outer diameter of the push member 84 at its distal end is much less than an outer diameter of the sponge 80. As such, the distal end of the push member 84 engages only a comparatively small portion of the proximal side of the sponge 80 when advancing the sponge 80 over the catheter 32 toward the wound. Nevertheless, as shown in FIG. 6, the sponge 80 preferably is comprised of a material that is generally cohesive so that the sponge 80 remains generally intact and moves as a unit as it is advanced over the catheter 32. As such, the push member 84 can advance the entire sponge 80 as a unit even though it contacts only a portion of one side of the sponge 80.

Preferably, the sponge 80 is at least partially coated with an adhesive so that the sponge will at least partially bond to the vessel wall 98. Alternatively, or in addition, flowable adhesive can be delivered into the field around the puncture wound before the sponge is advanced into contact with the vessel wall. Of course, the sponge can be delivered without using any adhesive.

Figure 7:
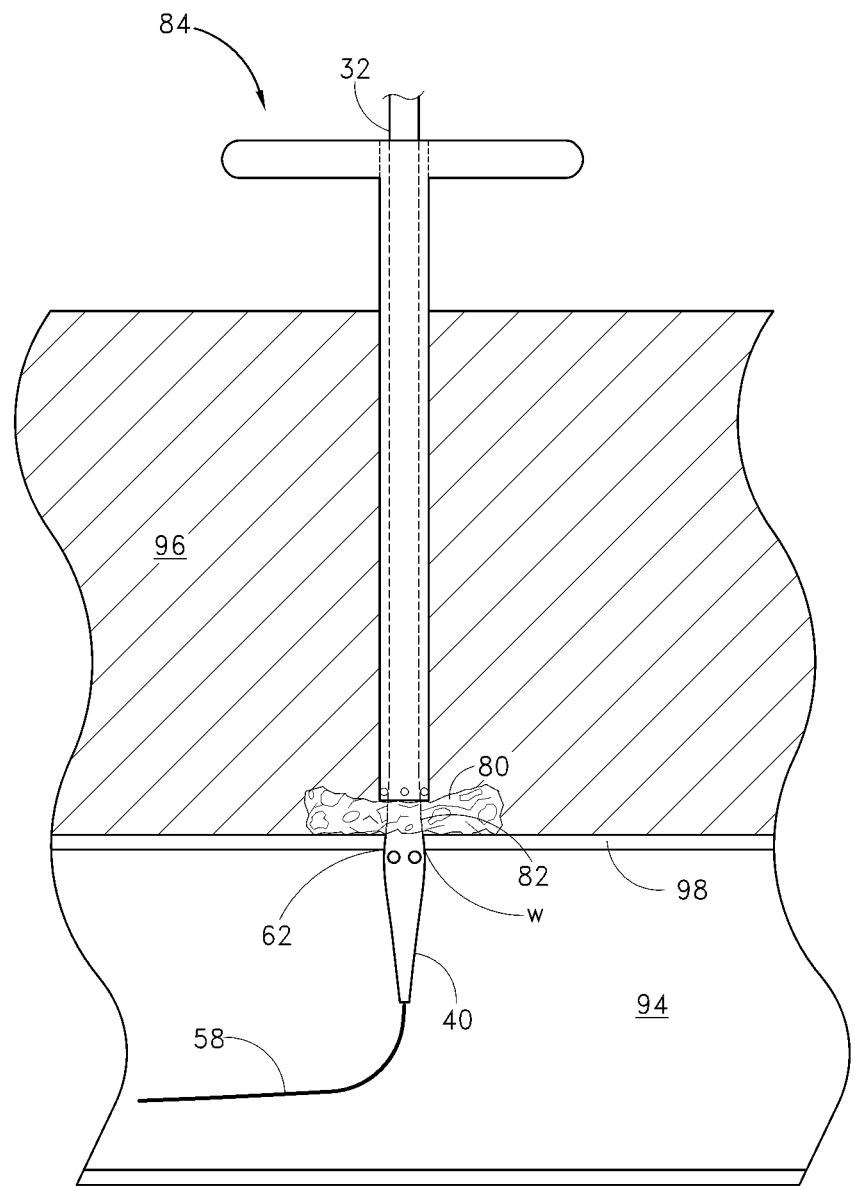
FIG. 7 shows the arrangement of FIG. 6, with the retractor arms removed.

The sponge 80 is preferably mounted onto the catheter 32 so as to substantially encircle the catheter 32. Thus, since the tip 40 of the catheter is disposed in the wound, the sponge 80 substantially surrounds the wound w when the sponge is positioned adjacent the vessel wall 98. When the sponge 80 is in place adjacent the wound w, the retractor 70 can be removed, as shown in FIG. 7. When the retractor 70 is removed, the surrounding body tissues 96 collapse around the sponge 80 and push member 84. The push member 84 holds the sponge 80 in position while body tissue 96 surrounds the sponge 80 and while the adhesive cures.

Figure 8:
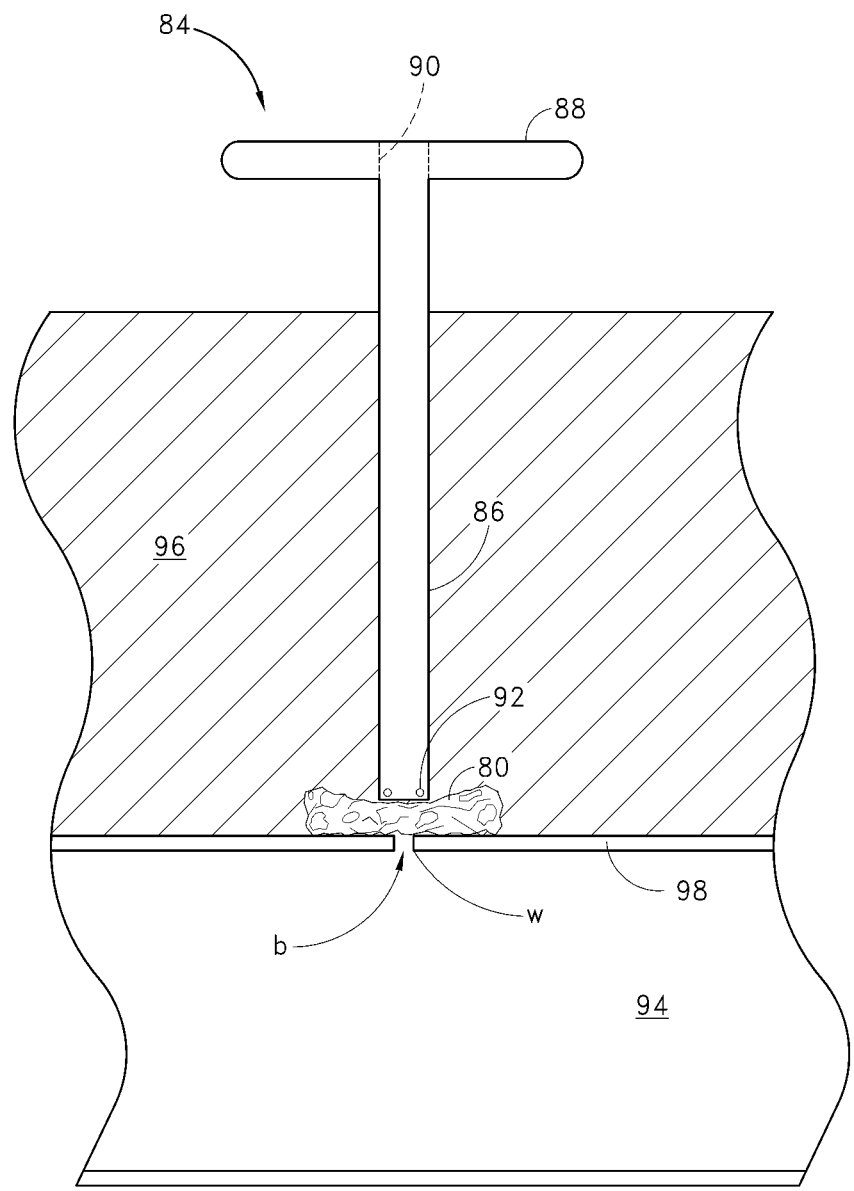
FIG. 8 shows the arrangement of FIG. 7 with the catheter and guidewire removed.

With reference next to FIG. 8, with the push member 84 in place, the catheter 32 and guidewire 58 can also be removed from the patient. The passage 82 through the sponge 80, which had been occupied by the catheter 32, collapses onto itself so that it is substantially closed. The vessel wound w is no longer plugged by the catheter 32, and it is anticipated that blood b from the vessel 94 will flow into the sponge 80, at least partially soaking the sponge 80. Although the retractor 70 is removed prior to the catheter 32 in the above-discussed embodiment, it is to be understood that, in another embodiment, the catheter may be removed prior to the retractor.

In still another embodiment, additional pressure can be applied to the push member 84 in order to at least partially block blood flow through the blood vessel 94. In this manner, the clinician can control how quickly blood will flow through the wound w and into the sponge 80. Of course, other methods and apparatus can be used to temporarily reduce or stop blood flow through the vessel.

In a preferred embodiment, the sponge 80 comprises a material made of or soaked in a hemostatic agent. The agent is specially adapted to aid blood clotting. Thus, blood that flows into the sponge will quickly become clotted, causing natural sealing of the wound through blood clotting. Sponge-like hemostasis agents are available and can include products such as Gelfoam™, Oxycell™ and Avitene™. Other appropriate hemostatic sponges may be impregnated with thrombin, a liquid clotting agent, to help accelerate blood clot formation. Another material that may advantageously be used is a collagen Ultrafoam™ sponge marketed by C.R. Bard/Davol, Inc. The Ultrafoam™ sponge is made from Avitene™ collagen, a natural clotting agent, and does not require the addition of thrombin. This reduces preparation time and the risk that a patient will experience a potentially hazardous reaction to bovine thrombin. Other medicants can also be included in the sponge. For example, antibiotic medicines, anti-inflammatory drugs, healing aids, and the like can be impregnated into the sponge material.

The sponge-like material is preferably soft and pliable and will conform to the structure of the blood vessel, the wound and the field around the blood vessel. Thus, the sponge-like material is specially suited for use in the confined space surrounding a vascular puncture. Additionally, the hemostatic sponge 80 will be held in place by the tissue 96 surrounding the puncture wound w, which tissue 96 collapses over the sponge 80 when tools such as the retractor 70 are removed.

Figure 9:
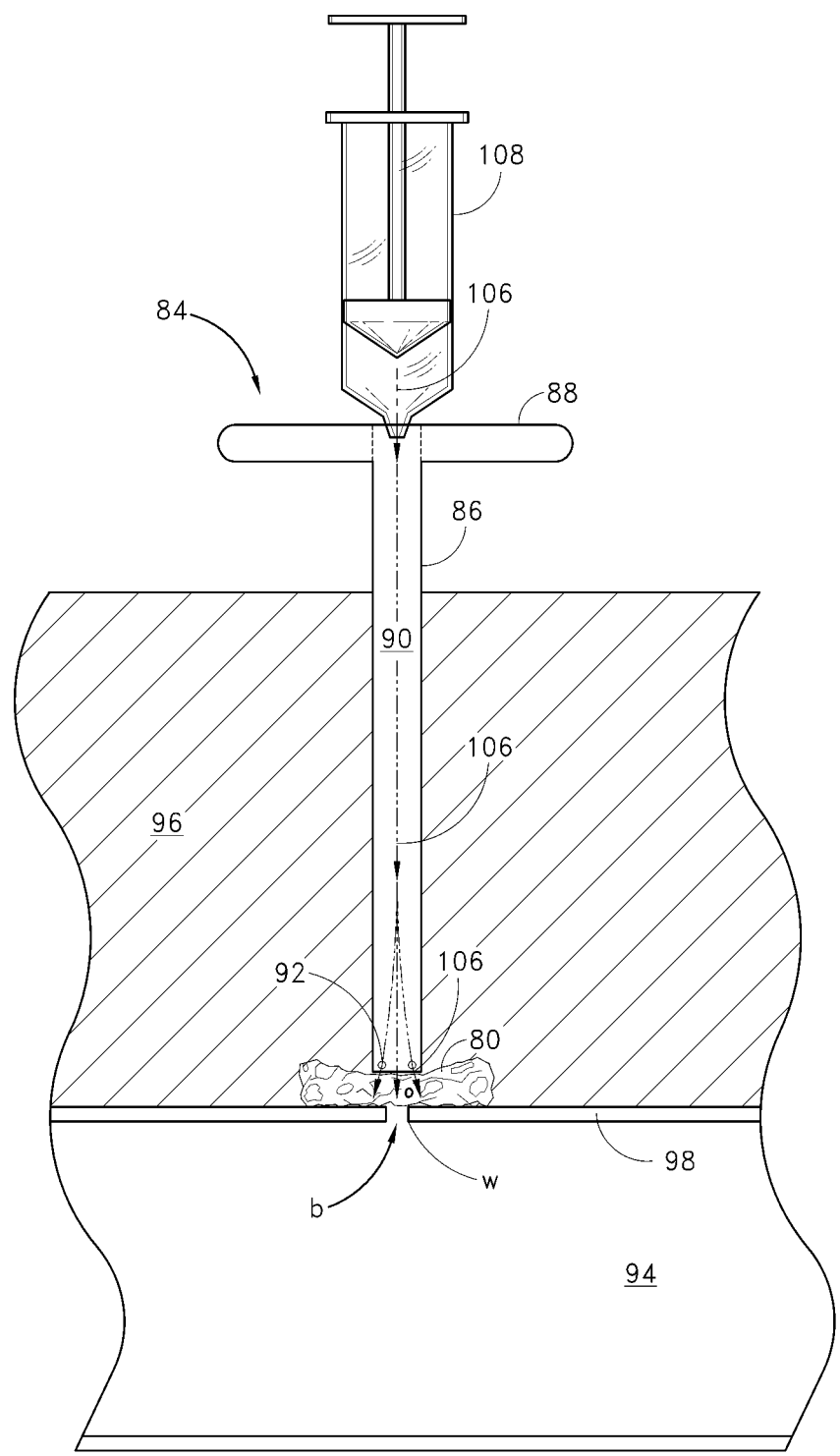
FIG. 9 shows the arrangement of FIG. 8, wherein a flowable adhesive is being delivered to the sponge.

To further help hold the sponge 80 in place, flowable adhesive 106 from a source of adhesive 108 can be delivered through the lumen 90 of the push member 84 and onto the sponge 80, as shown in FIG. 9. The adhesive 106 flows through the open distal end of the push member 84 and also through the holes 92 through the push member body portion 86. Upon curing, the adhesive 106 can form a sealing layer around and within the sponge 80, thus confining the blood b to the sponge area. This helps minimize bleeding and even further speeds clot formation. Adding adhesive 106 will also facilitate more complete closure of the passage through the sponge, which passage was vacated by the catheter 32. Further, the adhesive 106 will help hold the sponge 80 in place relative to the puncture wound w and the surrounding tissue 96.

As discussed above, prior to being advanced into contact with the blood vessel wall, the sponge 80 may be soaked in an adhesive or, more preferably, coated with a layer of adhesive. In this manner, adhesive distribution on the sponge can be controlled. By controllably applying a coating of adhesive around the outer surface of the sponge, the adhesive will bond the sponge to the area surrounding the blood vessel wound w, including the vessel 94 itself, and also can form a perimeter seal of the sponge when the adhesive cures. The coating of adhesive can act as a membrane confining the blood b to the sponge 80. It is to be understood that a coating of adhesive may be used instead of or in addition to applying additional adhesive 106 through the push member 84.

Various kinds of flowable adhesives may be acceptable for use with the sponge. For example, fibrin tissue sealants such as Tisseel®, which is available from Baxter Healthcare Corp., may be appropriate. Other commercially available adhesives that may be appropriate include Bioglue™, available from Cryolife, Inc., and Floseal™, which is available from Fusion Medical Technologies. Various cyanoacrylate adhesives are currently commercially available and can be used with this invention. Of course, any product that is capable of sealing the sponge or at least retarding blood flow through or beyond the sponge would be acceptable. It is also to be understood that certain adhesives will not require that the field and/or the outer wall of the blood vessel be cleared before the adhesive is injected.

Curing time and ease of use will vary depending on the adhesive used. For example, some adhesives cure to a malleable gel-like state within a few seconds, while others will cure directly to a hardened state in a few minutes. The time period for curing is chosen to allow the clinician to advance the sponge into position adjacent the wound and in contact with the artery, at which time the sponge will begin to be bonded to the vessel wall and substantially sealed by the adhesive. It should be appreciated that any acceptable adhesive having any acceptable curing time may be used.

The push member 84 may be kept in place for any reasonable time period in order to allow the adhesive 106 to cure. Also, multiple sponges can be used, if desired. Preferably, however, the adhesive 106 will cure sufficiently in about five minutes or less. Other tools, such as an ultraviolet light source or a heat application device, may be used to help speed adhesive curing.

Figure 10:
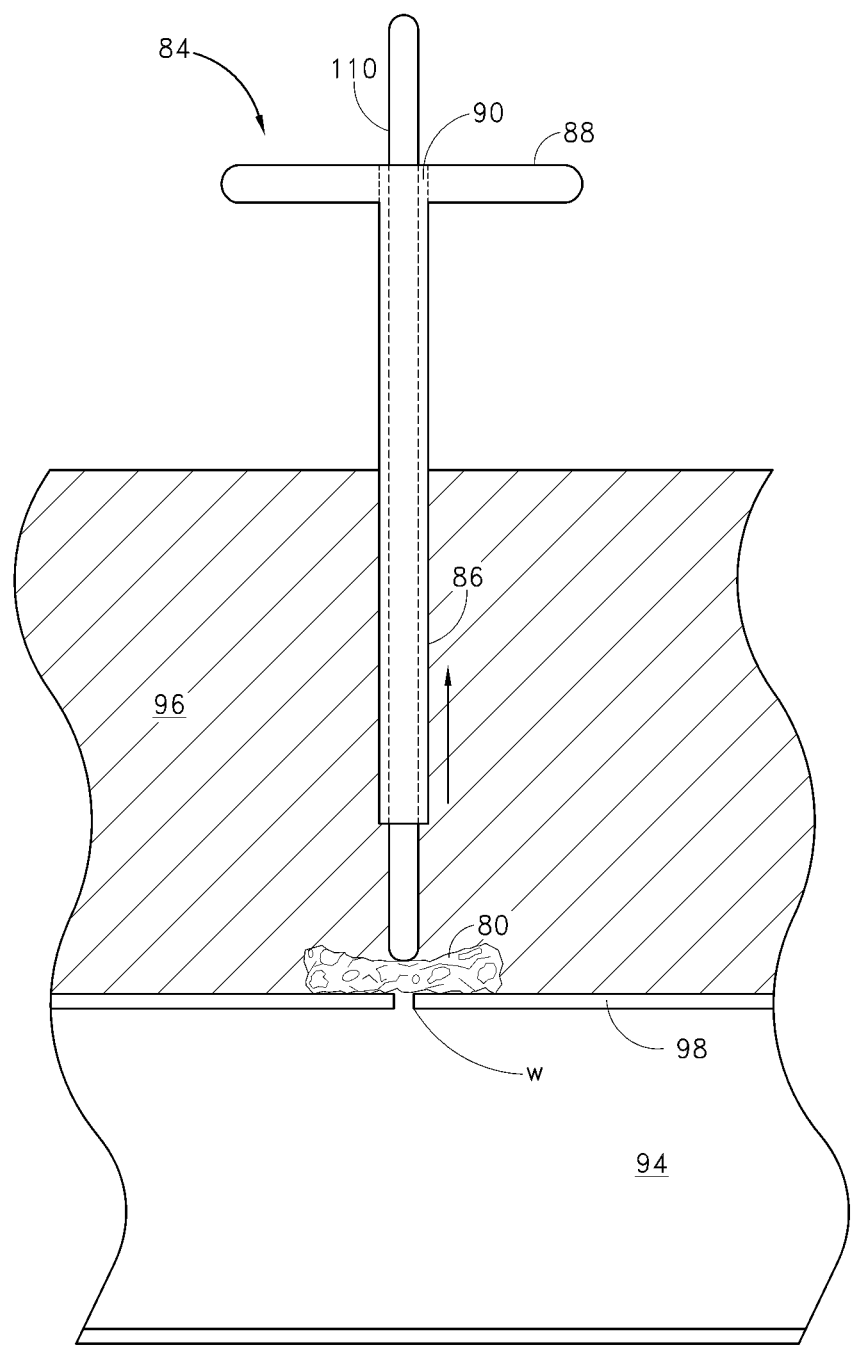
FIG. 10 shows the arrangement of FIG. 8, wherein the push member is being removed from the patient.
Figure 11:
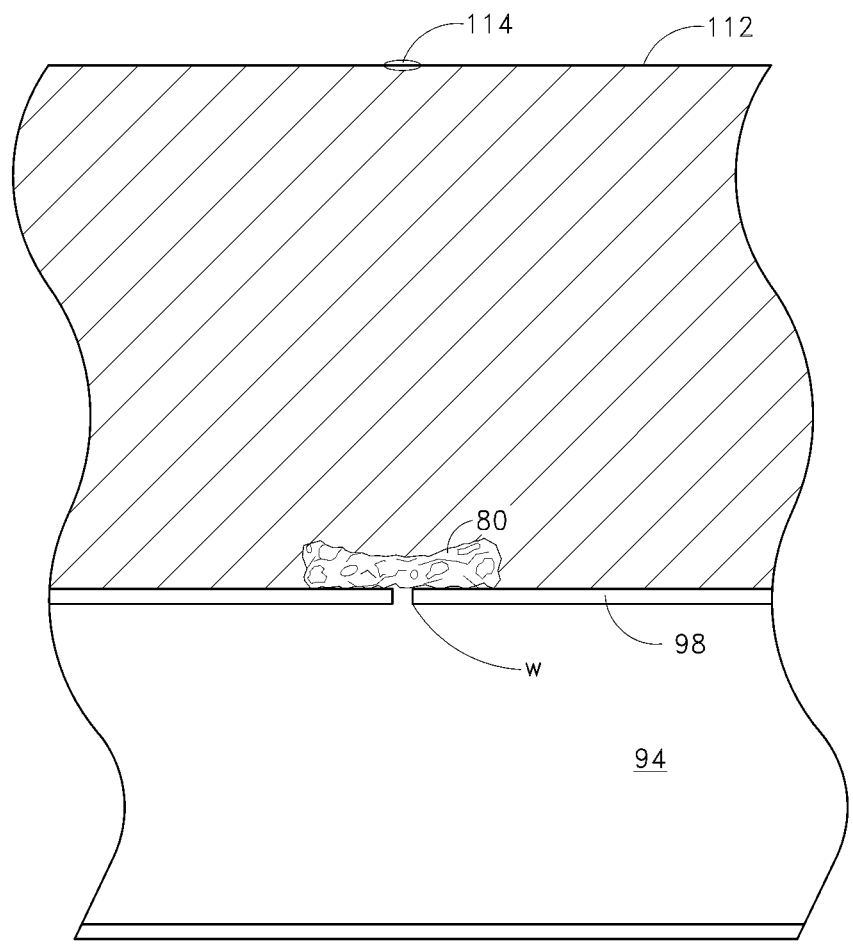
FIG. 11 shows a sealed puncture wound after treatment with an embodiment of the device and method.

Once the sponge 80 is correctly placed, the push member 84 can be removed. Removal of the push member 84 can be aided by a release rod 110 which, as shown in FIG. 10, is advanced through the push member lumen 90 and into contact with the sponge 80. The release rod 110 holds the sponge 80 in place as the push member 84 is withdrawn from the patient. Thus, the release rod 110 engages the sponge 80 so as to provide counter traction when the push member 84 is withdrawn. In this way, the push member 84 can be removed even if some adhesion occurs between the sponge 80 and the push member 84. With reference next to FIG. 11, once the release rod 110 is withdrawn, the patient's skin 112 is closed by any appropriate closure media such as, for example, sutures 114. The hemostatic sponge 80 is left in place. The body's natural blood clotting process will plug and repair the vascular wound w with the aid of the hemostatic sponge 80. Thus, healing will proceed without the danger of false aneurysms, missed or faulty wound closure, or the like.

As discussed above and shown in FIGS. 1 and 7, the hemostatic sponge 80 circumferentially surrounds the catheter 32, and the catheter 32 preferably extends through a puncture hole 82 through the sponge 80. When the catheter 32 is removed, however, the hole 82 remains. Sponges that are relatively elastic will spring back into place, filling the hole 82. However, some hemostatic sponge materials have relatively poor elastic resilience and mechanical strength. Such materials may not be able to spring back into place to fill the hole. This is problematic because the hole 82 is aligned with the blood vessel wound w; thus, blood b may flow substantially unimpeded through the hole 82, possibly leading to complications. Also, adhesive that is injected can possibly flow through the hole 82 in the sponge 80 and further through the wound w and into the bloodstream.

Figure 12:
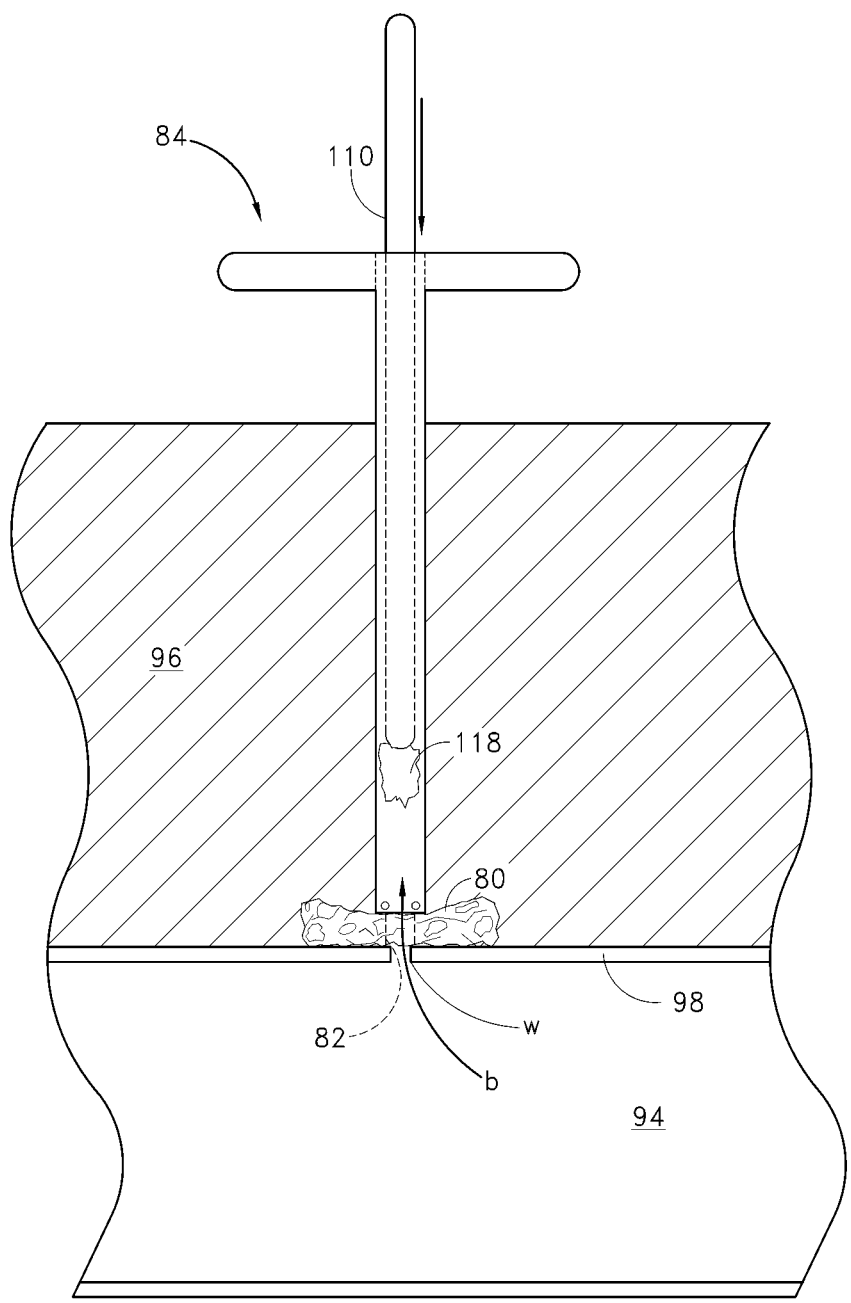
FIG. 12 shows an embodiment wherein an additional sponge is being advanced toward the wound.
Figure 13:
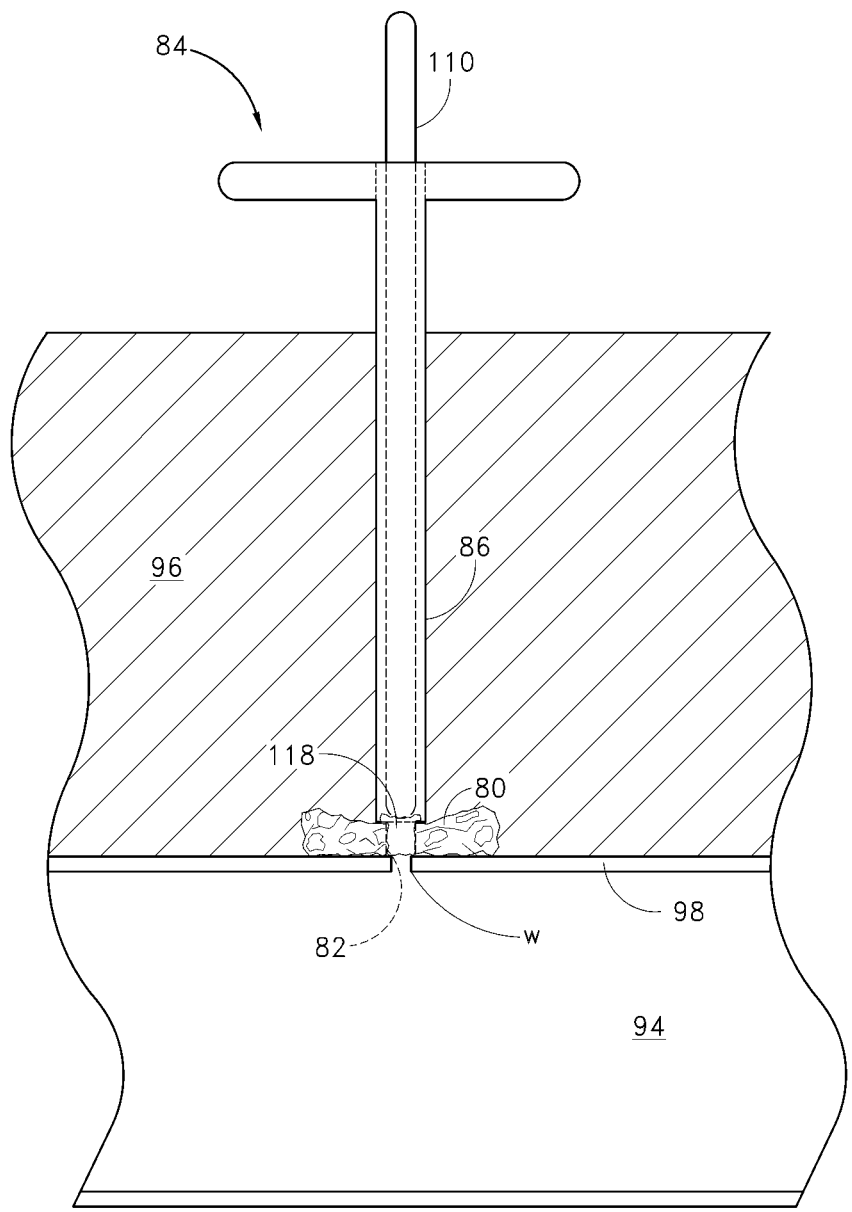
FIG. 13 shows the embodiment of FIG. 12 with the additional sponge in place.

Accordingly, in another embodiment depicted in FIGS. 12 and 13, the release rod 110 can be used to advance one or more additional hemostatic members 118 through the push member lumen 90 and into contact with the original sponge 80. The additional sponge material 118 can help further plug the hole 82 in the sponge 80 through which the catheter 32 was disposed, and will stem the flow of blood b with the hemostatic sponge material 118, which will facilitate blood clotting. The additional sponge material 118 will also plug the hole 82 left in the original sponge 80 so that adhesive that may be added later will be blocked from entering the wound w.

Figure 14:
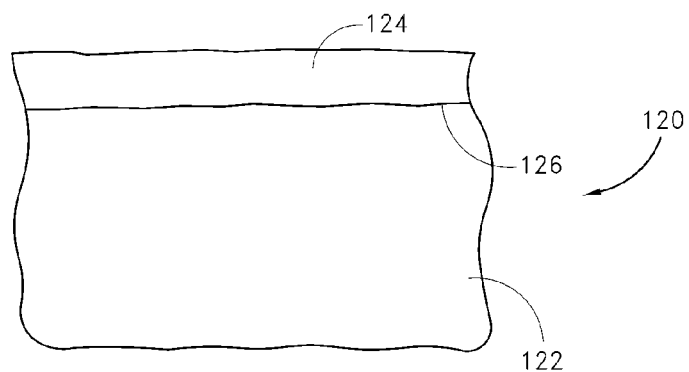
FIG. 14 shows another embodiment of a hemostatic sponge member.
Figure 15:
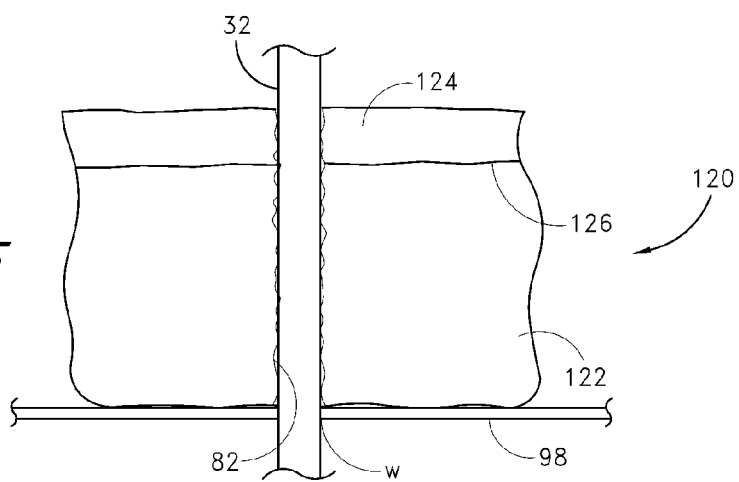
FIG. 15 shows the sponge member of FIG. 14 in contact with the vessel wall and having a catheter extending therethrough.
Figure 16:
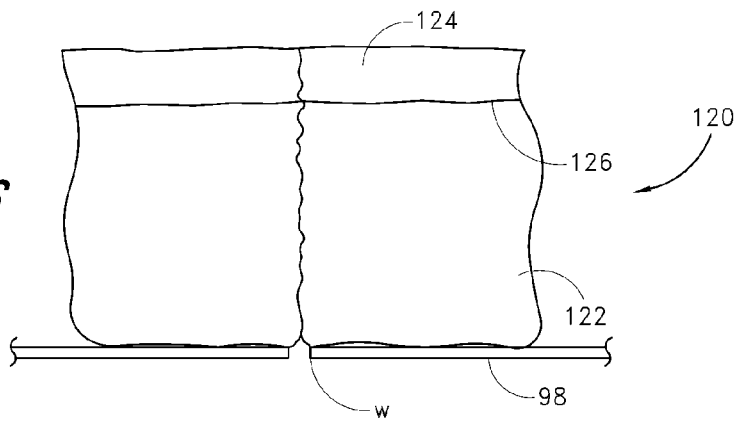
FIG. 16 shows the arrangement of FIG. 15 with the catheter removed.

With reference next to FIGS. 14-16, another embodiment of a hemostatic sponge member 120 comprises a hemostatic sponge layer 122 and a highly elastic layer 124. A layer of cement 126 attaches the hemostatic layer 122 to the elastic layer 124. Alternatively, the hemostatic layer 122 and elastic layer 124 can be integrally formed. As with the hemostatic sponge 80 described above, the hemostatic layer 122 comprises a hemostatic agent which facilitates and speeds blood clotting. The elastic layer 124 improves the overall elasticity and mechanical strength of the sponge 120. Preferably the elastic layer 124 comprises a polymer having relatively high elastic resilience and mechanical strength. Polymer elastomers such as polyurethane, SDS and silicon rubber can advantageously be used for the elastic layer 124. It is to be understood that the elastic layer 124 preferably is non-toxic. Also, it is not necessary for the elastic layer to include a hemostasis agent or any other medicament.

As discussed above, the catheter 32 preferably extends through a puncture hole 82 through the hemostatic sponge 120. With continued reference to FIG. 15, the elastic layer 124 is preferably oriented on a side of the sponge 120 away from the wound w, while the hemostatic sponge layer 122 is oriented so as to directly contact the blood vessel wall 98 and wound w. With specific reference to FIG. 16, when the catheter 32 is removed from the hemostatic sponge 120, the highly elastic layer 124 will immediately retract, substantially sealing the hole 82. Since the hemostatic sponge layer 122 is connected to the elastic layer 124, the sponge material 122 will also be retracted, closing the hole. Accordingly, not only will the hole be sealed, but the hemostatic material 122 will fill the hole 82 so as to be placed directly in the path of blood b coming from the vascular wound w. Accordingly, more thorough and speedier blood clotting is achieved.

In the embodiment illustrated in FIGS. 1-9, the catheter comprises a single-lumen catheter. In another embodiment (not shown), the elongate catheter has a first lumen comprising a tube that extends from the distal end opening to the proximal end opening and slidingly accommodates the guidewire therewithin. The outer wall of the catheter defines a second lumen that concentrically surrounds the first lumen. The holes through the outer wall of the catheter open into the second lumen. Additionally, an access lumen communicates with the second lumen. In this embodiment, the distal and proximal openings, which accommodate the guidewire, do not communicate with the second lumen, which lumen communicates with the source of suction through the access lumen. Accordingly, in this embodiment, there may be less of a chance that body fluids will be drawn into the catheter through the distal and proximal guidewire openings than in an embodiment employing a single lumen. However, the single-lumen catheter can be less expensive to manufacture and can be expected to have a smaller diameter than the dual-lumen catheter.

Portions of the above-described embodiments share certain aspects with the apparatus disclosed in co-pending U.S. application Ser. No. 09/325,982, filed on Jun. 4, 1999, now U.S. Pat. No. 6,287,322, which is hereby incorporated by reference in its entirety. FIGS. 28-31 and 48-50 of U.S. Pat. No. 6,287,322 show some embodiments of retractors and a catheter that may be used in accordance with certain embodiments.

Figure 17:
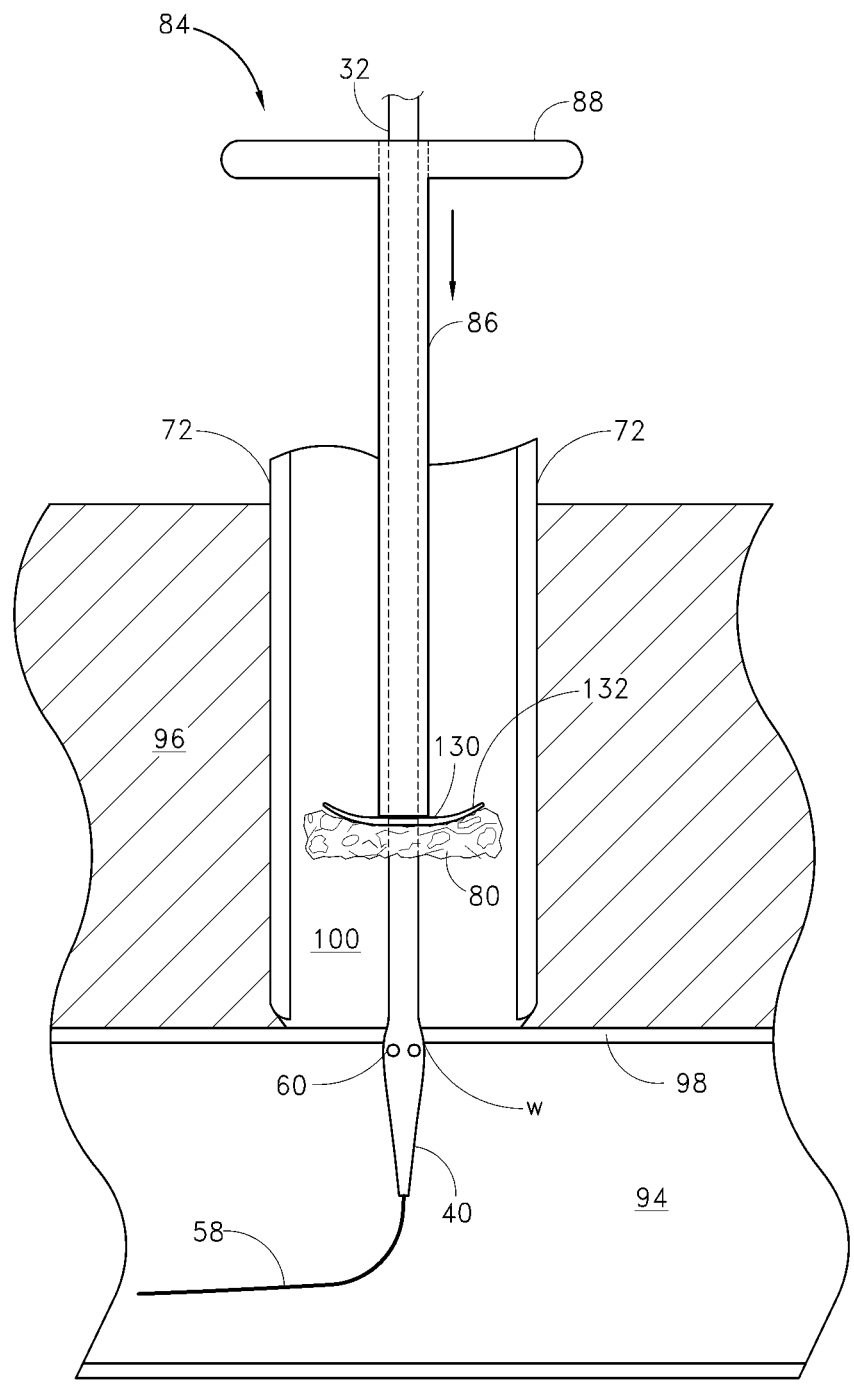
FIG. 17 shows an embodiment in which a lock member is provided proximal a hemostatic sponge member.
Figure 18:
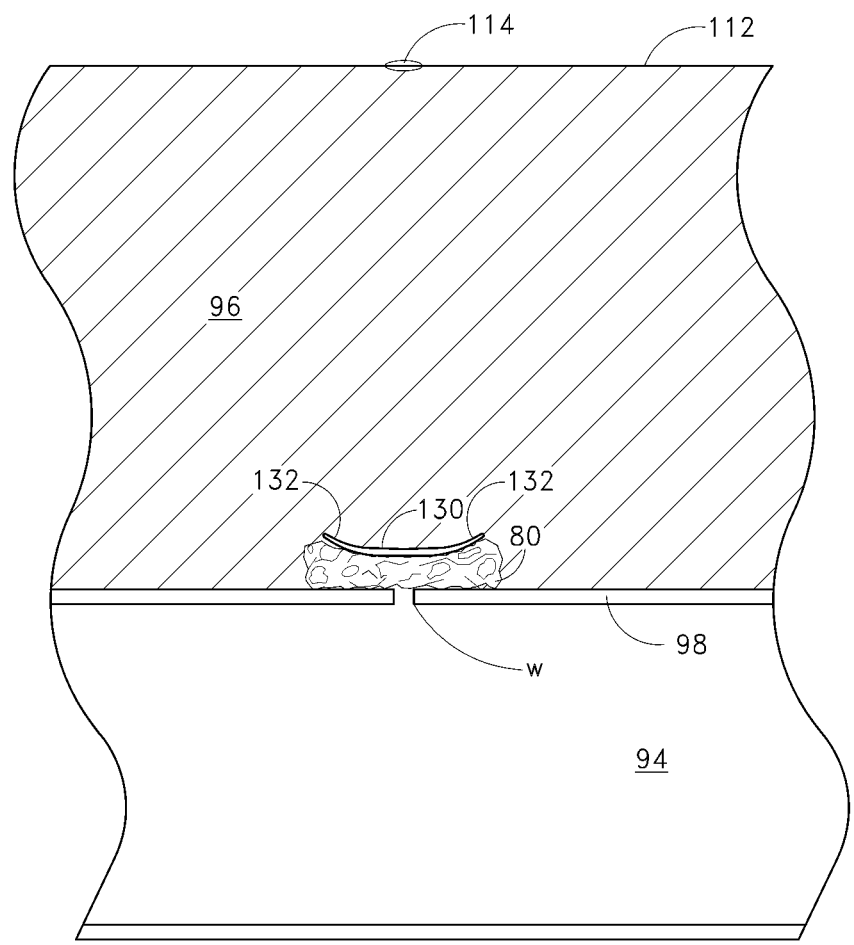
FIG. 18 shows a sealed puncture wound after treatment with the device of FIG. 12.

FIG. 17 shows another additional embodiment wherein a lock apparatus 130 is employed to help hold the sponge 80 in place against the artery wall 98. The lock apparatus 130 is preferably slidably disposed about the catheter 32 between the push member 84 and the sponge 80. The lock apparatus 130 accompanies the sponge 80 as it is advanced into position on the blood vessel wall 98 surrounding the vascular wound w. The lock apparatus 130 has arms that preferably are configured to allow movement through tissue 96 toward the wound w, but resist movement of the apparatus 130 in the direction away from the wound w. Thus, the lock apparatus 130 holds the sponge 80 tightly in place adjacent the wound w as shown in FIG. 18.

It is to be understood that several forms of the lock apparatus may be advantageously employed. For example, in the illustrated embodiment, the lock apparatus 130 has swept-back arms 132 that are adapted so that the apparatus 130 can be advanced through a tissue 96 toward the vascular wound w, but cannot be moved away from the vascular wound w because the arms 132 will engage the surrounding tissue 96. In another embodiment, selectively actuable arms may be provided within the lock apparatus. A trigger may be provided so that the arms will extend into the surrounding tissue when the trigger is actuated, thus locking the device in place and holding the sponge next to the vascular wound.

The lock apparatus is preferably formed of a material that can be absorbed by the body over time. However, other materials, such as stainless steel, can be advantageously used.

Figure 19:
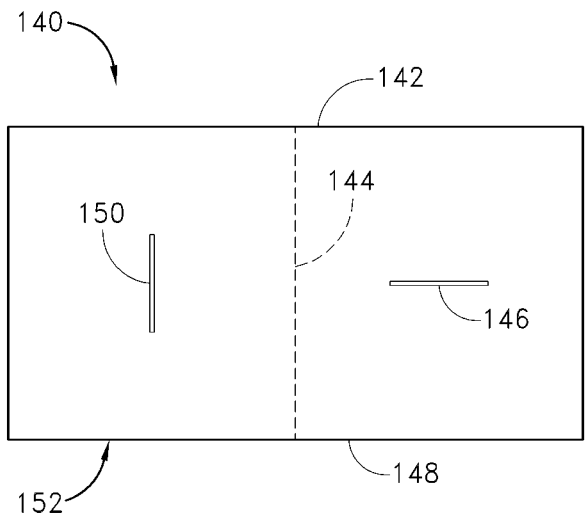
FIG. 19 shows a schematic view of an unfolded two-layer patch.
Figure 20:
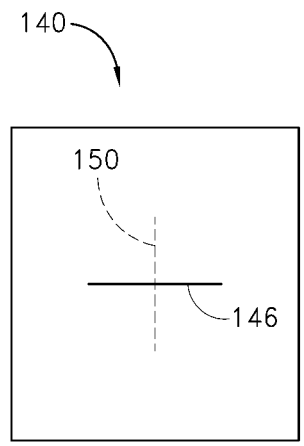
FIG. 20 shows the patch of FIG. 19 in a folded position.
Figure 21:
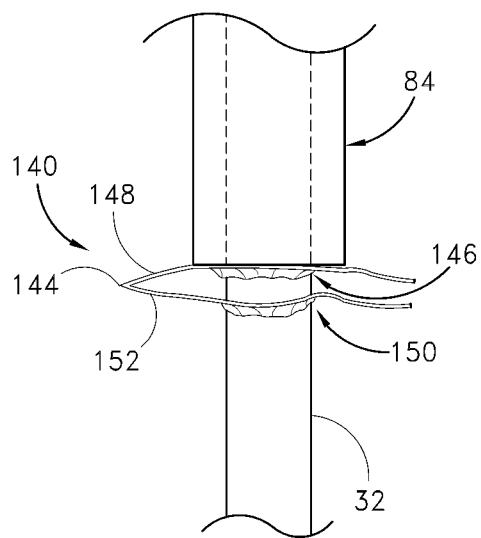
FIG. 21 shows the patch of FIG. 19 slidably mounted onto a catheter and being advanced by a push member.

In a further additional embodiment illustrated in FIGS. 19-21, a multi-layer patch 140 is used in addition to or instead of the sponge 80. The patch 140 may be soaked or coated with a hemostatic agent and/or adhesive and is specially adapted to be advancable over the catheter 32 and to cover the vascular wound w. As shown in FIG. 19, the patch 140 preferably comprises a single piece of material 142 having a fold line 144 disposed roughly down the middle thereof. A first slit 146 is provided in a first half 148 of the patch 140 and a second slit 150 is provided in a second half 152 of the patch 140. Preferably, the second slit 150 is substantially normal to the first slit 146. The patch material 142 is folded over itself as shown in FIG. 20 and is threaded over the catheter 32 as shown in FIG. 21. The catheter 32 fits through each of the slits 146, 150, which provide room for the catheter 32 to slidingly fit therethrough. However, as the patch 140 is advanced into position and the catheter 32 is removed from the patch, the slits 146, 150 overlap each other, leaving only a small hole, if any. Adhesive can be applied over the small hole and/or between the halves to ensure sealing of the patch and closure of the wound.

A number of other embodiments may be employed that combine various aspects that have been discussed above. For example, the multi-layer patch 140 of FIG. 17 may be bonded to the artery wall 98 using an adhesive applied to the base of the patch and then a sponge may be advanced over the patch, or vice versa. Additionally, rather than the two-arm retractor 70 disclosed herein, other means may be used for providing access to the blood vessel 94. For instance, access and location may be provided by a cannula, balloon, or the like. Still further, in some embodiments, an elastic and conformable sponge can be positioned adjacent the wound by being advanced over the catheter, or even over a bare guidewire, without using any additional access-providing device.

Although this invention has been disclosed in the context of certain preferred embodiments and examples, it will be understood by those skilled in the art that the present invention extends beyond the specifically-disclosed embodiments to other alternative embodiments and/or uses of the invention and obvious modifications and equivalents thereof. In addition, while a number of variations have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed modular arrangement and method. Thus, it is intended that the scope of the present invention should not be limited by the particular disclosed embodiments described above, but should be determined only by a fair reading of the claims that follow.

What is claimed is:

1. A method for closing a wound in a blood vessel of a patient, comprising:
   providing a guidewire extending through the wound and out of the patient;
   providing a catheter adapted to accommodate the guidewire and comprising a lumen, the catheter having at least one hole formed through a side of the catheter, the at least one hole communicating with the lumen;
   providing a source of suction;
   placing the lumen into communication with the source of suction;
   providing a retractor having a plurality of elongate refractor arms;
   coupling the retractor to the catheter so that a distal end of each refractor arm is positioned proximal of the hole a distance at least the same as a thickness of a wall of the artery;
   mounting a hemostatic material onto the catheter;
   threading the catheter over the guidewire;
   advancing the catheter and retractor over the guidewire until blood is drawn through the at least one hole in the lumen;
   actuating the retractor to at least partially provide access to an outer wall of the artery surrounding the wound;
   advancing the hemostatic material over the catheter into contact with the artery; and
   removing the retractor, catheter and guidewire.

2. The method of claim 1, further comprising holding the hemostatic material in position until it is anticipated that the hemostatic material has become at least partially soaked with blood.

3. The method of claim 1, further comprising applying a flowable adhesive to the hemostatic material before the material is advanced into contact with the blood vessel.

4. The method of claim 1, further comprising applying adhesive to a portion of the blood vessel adjacent the puncture wound prior to advancing the hemostatic material into contact with the blood vessel.

5. The method of claim 1, further comprising applying a flowable adhesive to the hemostatic material after the material has been advanced into contact with the blood vessel.

6. The method of claim 1, further comprising providing a viewing portion communicating with the lumen and adapted to enable identification of bodily fluids drawn through the lumen.

7. The method of claim 6, wherein the catheter is substantially transparent, and the viewing portion comprises the catheter.

8. The method of claim 1, further comprising providing a push member adapted to advance the hemostatic material over the catheter.

9. The method of claim 8, further comprising holding the hemostatic material in position using the push member.

10. A method for closing a vascular wound, comprising:
    locating the wound;
    positioning a surgical implement so that a portion of the implement extends through the wound and a portion extends out of the wound;
    providing a hemostatic material;
    positioning the hemostatic material about the implement; and
    advancing the hemostatic material over the surgical implement so that the hemostatic material is disposed adjacent the wound.

11. The method of claim 10, further comprising providing an access passage to the wound.

12. The method of claim 11, wherein the access passage is provided by a plurality of elongate retractor arms.

13. The method of claim 11, further comprising clearing a field surrounding the wound prior to positioning the hemostatic material.

14. The method of claim 10, further comprising holding the hemostatic material in place on the wound as the material becomes at least partially soaked with blood from the wound.

15. The method of claim 10, wherein the surgical implement comprises a guidewire and an elongate catheter, wherein a tip of the catheter is extending through the wound.

16. The method of claim 15, wherein the catheter is removed from the wound after the hemostatic material is disposed adjacent the wound.

17. The method of claim 10, wherein the hemostatic material is positioned on the surgical implement by poking the implement through the hemostatic material.

18. The method of claim 17, wherein the hemostatic material comprises a first layer and a second layer, the first layer being highly elastic, the second layer comprising a hemostasis agent.

19. The method of claim 10, further comprising applying adhesive to the hemostatic material.

20. The method of claim 10, further comprising providing a push member adapted to slide over the surgical implement and using the push member to advance the hemostatic material over the implement, wherein the push member comprises a lumen, and the lumen substantially surrounds the surgical implement, advancing a second hemostatic material through the push member lumen into contact with the first hemostatic material, and inserting flowable adhesive through the push member lumen into contact with the hemostatic material.

* * * * *